US009248319B2

(12) United States Patent
Pisula et al.

(10) Patent No.: US 9,248,319 B2
(45) Date of Patent: Feb. 2, 2016

(54) COMPOSITE PARTICLES FOR USE IN ORAL HYGIENE

(75) Inventors: Wojciech Pisula, Mainz (DE);
Stephanie Schäffer, Hanau (DE); Juri Tschernjaew, Aschaffenburg (DE);
Arnold Storeck, Frankfurt (DE); Rainer Hahn, Büdingen (DE)

(73) Assignee: Evonik Degussa, Essen (DE)

( * ) Notice: Subject to any disclaimer, the term of this patent is extended or adjusted under 35 U.S.C. 154(b) by 629 days.

(21) Appl. No.: 12/851,623

(22) Filed: Aug. 6, 2010

(65) Prior Publication Data

US 2011/0033511 A1  Feb. 10, 2011

(30) Foreign Application Priority Data

Aug. 8, 2009  (DE) .......................... 10 2009 036 767

(51) Int. Cl.
| | |
|---|---|
| A61K 8/00 | (2006.01) |
| A61Q 11/00 | (2006.01) |
| A61K 8/02 | (2006.01) |
| A61K 8/25 | (2006.01) |
| A61K 8/27 | (2006.01) |
| A61K 8/34 | (2006.01) |
| A61K 8/73 | (2006.01) |

(52) U.S. Cl.
CPC .............. *A61Q 11/00* (2013.01); *A61K 8/0279* (2013.01); *A61K 8/25* (2013.01); *A61K 8/27* (2013.01); *A61K 8/347* (2013.01); *A61K 8/733* (2013.01); *A61K 2800/28* (2013.01); *A61K 2800/412* (2013.01); *A61K 2800/56* (2013.01)

(58) Field of Classification Search
None
See application file for complete search history.

(56) References Cited

U.S. PATENT DOCUMENTS

| | | | |
|---|---|---|---|
| 4,011,898 A | 3/1977 | Hubbard | |
| 4,053,851 A | 10/1977 | Krupke | |
| 4,065,564 A | 12/1977 | Miles et al. | |
| 4,073,880 A | 2/1978 | Pader et al. | |
| 4,115,130 A | 9/1978 | Crump et al. | |
| 4,278,655 A | 7/1981 | Elmi | |
| 4,414,005 A | 11/1983 | Bievre et al. | |
| 4,938,955 A | 7/1990 | Niira et al. | |
| 5,084,440 A | 1/1992 | Baudin et al. | |
| 5,500,138 A | 3/1996 | Bacon et al. | |
| 5,776,240 A | 7/1998 | Deller et al. | |
| 6,294,505 B1 | 9/2001 | Luers et al. | |
| 6,905,698 B1 | 6/2005 | Aldcroft et al. | |
| 2001/0026802 A1 | 10/2001 | Price et al. | |
| 2002/0103219 A1* | 8/2002 | Jacob ........................... | 514/291 |
| 2004/0047792 A1 | 3/2004 | Schubert et al. | |
| 2004/0142170 A1 | 7/2004 | Prabhu et al. | |
| 2007/0036843 A1 | 2/2007 | Hirsh et al. | |
| 2007/0275068 A1* | 11/2007 | Martens et al. ................ | 424/484 |
| 2008/0058459 A1 | 3/2008 | Brand et al. | |
| 2008/0279947 A1 | 11/2008 | Nowak et al. | |
| 2010/0026802 A1 | 2/2010 | Titus et al. | |
| 2011/0030578 A1 | 2/2011 | Schulz et al. | |
| 2011/0033511 A1 | 2/2011 | Pisula et al. | |
| 2011/0037021 A1 | 2/2011 | Tschernjaew et al. | |

FOREIGN PATENT DOCUMENTS

| | | |
|---|---|---|
| CA | 2438438 | 2/2005 |
| CH | 573212 | 3/1976 |
| DE | 102008000290 | 8/2009 |
| DE | 102009028255 | 2/2011 |
| DE | 102009036767 | 2/2011 |
| EP | 0005302 | 11/1979 |
| EP | 0170386 | 12/1983 |
| EP | 0454881 | 11/1991 |
| EP | 0341383 | 6/1992 |
| EP | 0798348 | 12/1998 |
| EP | 0725037 | 3/2001 |
| EP | 1241135 | 9/2002 |
| EP | 0922671 | 10/2003 |
| EP | 1398301 | 9/2007 |
| GB | 2018590 | 7/1982 |
| JP | 2002212042 | 7/2002 |
| JP | 2008533260 | 8/2008 |
| WO | 97/29157 | 8/1997 |
| WO | 00/11949 | 3/2000 |
| WO | 00/51724 | 9/2000 |
| WO | 01/58416 | 8/2001 |
| WO | 02/098998 | 12/2002 |
| WO | 03/033027 | 4/2003 |
| WO | 03/082360 | 10/2003 |
| WO | 2004/072153 | 8/2004 |
| WO | 2005/012175 | 2/2005 |
| WO | 2006/004481 | 1/2006 |

(Continued)

OTHER PUBLICATIONS

United States Patent Office Action for U.S. Appl. No. 12/850,775 dated Aug. 15, 2012 (16 pages).
Park, D.J. et al., "Controlled Release of Pesticides from Microparticles," Controlled-release Delivery Systems for Pesticides (H.B. Scher, editor), Marcel Dekker Inc., New York (1999) 89-136.
European Search Report for Application No. 10170359 dated Oct. 14, 2010 (6 pages).
International Preliminary Report on Patentability for Application No. PCT/EP2009/051137 dated Sep. 10, 2010 (9 pages).

(Continued)

*Primary Examiner* — Snigdha Maewall
(74) *Attorney, Agent, or Firm* — Michael Best & Friedrich LLP

(57) ABSTRACT

The present invention relates to functional composite particles for the oral care sector, more particularly for toothpastes and mouthwashes, which are charged with active ingredients which ensure a long-term antimicrobial or antibacterial effect in the oral cavity and hence reduce the formation of plaque and halitosis. The invention further relates to a process for producing these composite particles and also to their use for producing oral hygiene articles.

19 Claims, 6 Drawing Sheets

(56) References Cited

FOREIGN PATENT DOCUMENTS

| WO | 2006/111761 | 10/2006 |
|----|-------------|---------|
| WO | 2007/024265 | 3/2007 |
| WO | 2007/030389 | 3/2007 |
| WO | 2007/048464 | 5/2007 |
| WO | 2008/013757 | 1/2008 |
| WO | 2008/025538 | 3/2008 |
| WO | 2009/100995 | 8/2009 |

OTHER PUBLICATIONS

Translation of International Preliminary Report on Patentability for Application No. PCT/EP2009/051137 dated Dec. 9, 2010 (10 pages).
International Search Report for Application No. PCT/EP2009/051137 dated Aug. 10, 2010 (5 pages).
United States Patent Office Action for U.S. Appl. No. 12/867,493 dated Jun. 7, 2013 (8 pages).
United States Patent Office Action for U.S. Appl. No. 12/850,775 dated Mar. 6, 2013 (6 pages).
United States Patent Office Final Rejection for U.S. Appl. No. 12/867,493 dated Sep. 19, 2013 (8 pages).
European Search Report for Application No. 10171251 dated Feb. 5, 2015 (8 pages).
Japanese Patent Office Action for Application No. 2010-178933 dated Jul. 22, 2014 (5 pages—English translation).

* cited by examiner

COMPOSITE PARTICLES FOR USE IN ORAL HYGIENE

CROSS-REFERENCE TO RELATED APPLICATIONS

This patent application claims priority to German Patent Application No. 102009036767.5, filed Aug. 8, 2009, the disclosure of which is incorporated by reference herein in its entirety.

INTRODUCTION

The present invention relates to functional composite particles for the oral care sector, more particularly for toothpastes and mouthwashes, which are charged with active ingredients which ensure a long-term antimicrobial or antibacterial effect in the oral cavity and hence reduce the formation of plaque and halitosis. The invention further relates to a process for producing these composite particles and also to their use for producing oral hygiene articles.

The addition of substances having antibacterial/antimicrobial properties to toothpastes and mouthwashes, and the effect thereof, are well known. However, the effect of the active substances is only short-term, since the concentration of the substance in question drops rapidly following oral hygiene, and microbial development and bacterial growth set in again immediately. In this context it has been found that commercial oral care products display only a very limited long-term effect in the oral cavity and that, for example, a large proportion of the active ingredients is removed from the mouth by rinsing with water after cleaning the teeth, for example, or by drinking or by consuming food. As a result of this, for example, mouth odour cannot be prevented over a prolonged period.

In order to achieve a sustained antibacterial or antimicrobial effect, these active ingredients must be localized in the oral cavity and subsequently released in a uniform way over a long period, directly in the oral cavity, in a defined concentration.

To date the active substances have generally been introduced by supporting and encapsulation on microparticles, which are in turn introduced into the oral region via the toothpaste or mouthwash. Thus, for example, US 2007/0036843 discloses compositions for oral use with delayed release of active ingredient. WO 2007/024265 and WO 2008/013757 disclose compositions for oral hygiene that are based on polymeric supports. WO 01/58416 discloses a toothpaste composition having different composite particles, some of which comprise active ingredients. WO 2006/111761 as well discloses oral hygiene articles comprising particulate carrier materials, charged with active ingredient, which are intended to ensure delayed release of the active ingredients. The approaches described in the documents cited above are not suitable for ensuring a sufficient long-term effect of the oral hygiene articles. In these approaches, indeed, the aim is to improve the delayed release of active ingredient from a support material. This is of no avail, however, if the particles are flushed from the oral cavity after just a short time. Furthermore, the particles used in the prior art are often so large as to produce a "sandy" sensation in the mouth.

DETAILED DESCRIPTION

Figure 1:
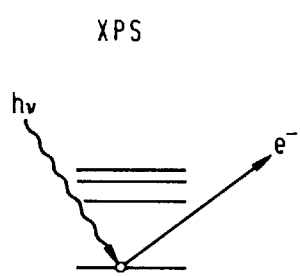
FIG. 1 depicts the principle of X-ray photoelectron spectrometry XPS/ESCA.

It was an object of the present invention, therefore, to provide innovative composite particles which allow an improved long-term effect of the active ingredients they comprise. A further aim is to provide a process for producing these active ingredients.

One specific object was to improve the long-term antimicrobial or antibacterial effect of active ingredients in the oral cavity.

Further objects, not explicitly stated, will become apparent from the overall context of the description, examples and claims that follow.

The inventors have surprisingly found out that the basic precondition for a sufficient long-term effect—namely the sufficiently long remanence of the active ingredients in the oral cavity—can be achieved, on the one hand, through a high level of interaction of the composite particles with the mucosa occurring in the mucous membranes of the mouth. On the other hand, however, the inventors have also found out that composite particles—when they are of a particular size—can be lodged between the teeth and in small hollows in the oral cavity and hence remain in the oral cavity over a relatively long period of time. These two effects can of course be combined, leading to particular advantages. The aforementioned effects, lastly, can be increased still further when the composite particles not only remain for a sufficiently long time in the oral cavity but also themselves ensure delayed release of active ingredient. Through the use of tailored composite particles, therefore, it is possible to ensure a significant improvement in the long-term effect of oral care products.

The present invention accordingly provides composite particles as additive for toothpaste and mouthwash, characterized in that they comprise
 a porous carrier of amorphous $SiO_2$, having an average particle size of 3 to 50 µm, preferably 4 to 40 µm, more preferably 5 to 30 µm, very preferably 6 to 25 µm, and a specific surface area of between 50 and 550 $m^2/g$, preferably 100 to 500 $m^2/g$, more preferably 150 to 500 $m^2/g$ and at least one envelope material,
the envelope material, following activation in the oral chamber, releasing an active substance, and/or the composite particles further comprising at least one active substance.

The invention further provides a process for producing the composite particles of the invention, characterized in that at least one porous amorphous silicon dioxide is contacted with at least one envelope substance and/or with at least one active ingredient.

The present invention further provides for the use of the composite particles of the invention for producing articles for oral hygiene.

The present invention, finally, provides oral hygiene articles, preferably toothpaste, mouthwash, mouth gel or mouth spray, comprising at least one composite particle of the invention, preferably in a fraction of 5% to 15% by weight.

Further subject matter of the present invention will become apparent from the overall context of the description, examples and claims below.

An advantage of the composite particles of the invention is that owing to the low particle size they do not produce a "sandy" sensation in the mouth. Furthermore, this small particle size ensures that the particles can lodge in "pockets" in the oral chamber and the particles therefore remain in the oral chamber for a sufficiently long time.

Where mucoadhesive envelope substances are used, the adhesion in the oral cavity is improved still further.

Through the choice of a suitable silicon dioxide or mixture of different silicon dioxide particles as carrier material it is possible to vary, for example, the diffusion of the active ingredient from the pores of the carrier. Furthermore, through the choice of the envelope material, it is also possible to vary the release mechanism, and so the composite particles of the invention can be adapted very flexibly to the requirements of the particular active ingredients.

Through the choice of silicon dioxides as carrier material it is possible to achieve not only the aforementioned flexibility but also high mechanical stability on the part of the composite particles, with the consequence, for example, that when incorporated into toothpastes or mouthwash, or when cleaning the teeth with a toothbrush, they persist without losing their capacity for delayed release of active ingredient.

The composite particles of the invention can be charged with a multiplicity of different active ingredients, and so can be employed universally.

The composite articles of the invention also have the advantage that they allow continuous release of active ingredient over a number of hours in the oral cavity.

The subject matter of the present invention is described in detail below. In the context of the present invention, the terms "envelope substance", "envelope material" and "protective substance" are used synonymously.

The terms "active ingredient" and "active substance" are likewise used synonymously and refer to entities capable of producing an antibacterial and/or antimicrobial effect in the oral cavity or which propagate a particular odour and/or a particular flavour in the oral cavity.

The composite particles of the invention comprise a carrier material composed of porous $SiO_2$, preferably amorphous $SiO_2$, more preferably of precipitated silica, fumed silica, silica prepared on the basis of fumed silica, or silica gel, or hybrid forms of these. It is especially preferred to use precipitated silicas according to EP 1398301 A2 or EP 1241135 A1 or EP 1648824 A1 or EP 0798348 A1 or EP 0341383 A1 or EP 0922671 A1. The subject matter of said applications is hereby incorporated explicitly into the present specification.

It is particularly preferred, moreover, to use silicon dioxides which have been developed especially as abrasive or thickening components for toothpaste formulations. These silicon dioxides have the advantage that they can be incorporated particularly well into toothpaste formulations. Examples thereof are those known under the brand names Sident® from Evonik Degussa or Tixosil® from Rhodia Chimie or Zeodent® from Huber. Silica gels for use as a filler for toothpastes have likewise been available on the market for a long time. As well as the aforementioned silicon dioxides, it is also possible to use those which have been developed as a carrier material, such as various Sipernats® from Evonik Degussa. Particular preference is given to using Sident® 22S and/or Sipernat® 50S from Evonik Degussa.

Likewise with preference it is possible to use specially spray-dried granules of fumed silicon dioxide. Very particularly preferred are those sold under the brand name AEROPERL® by Evonik Degussa; AEROPERL® 300/30 is especially preferred. The preparation of such AEROPERL® products from fumed silicon dioxide is described in EP0725037, whose content is hereby explicitly adopted into the description of the present invention.

It is important, however, that the silicon dioxides used in accordance with the invention have an average particle size $d_{50}$ of 3 to 50 µm, preferably 4 to 40 µm, more preferably 5 to 30 µm, very preferably 6 to 25 µm, especially preferably 6 to 20 µm, and very preferably 6 to 14 µm. This ensures that there is no "sandy" sensation produced in the mouth on application. Furthermore, this particle size ensures that the pores in the interior of the particles are not too long, thus allowing sufficiently rapid absorption of active ingredient and envelope substance.

In order to possess a sufficient carrier capacity, the silicon dioxides of the invention have a BET surface area of 50 to 550 $m^2/g$, preferably 100 to 500 $m^2/g$, more preferably 150 to 500 $m^2/g$.

In one preferred embodiment the silicas of the invention have a DBP number of 200 to 400 g/100 g, preferably 250 to 350 g/100 g. The DBP number is a measure of the dispersibility of the silicon dioxide. Too high a DBP number, moreover, leads to excessive thickening of the toothpaste.

It is likewise preferred if, when used in the toothpaste formulation, the silicon dioxides used in accordance with the invention have a refractive index of 1.43 to 1.47, preferably 1.44 to 1.46 and very preferably 1.45 to 1.46. The refractive index ought to be as close as possible to the refractive index of the toothpaste in order to avoid unwanted turbidities therein.

With very particular preference the carrier materials have two or more of the aforementioned physicochemical properties in combination, and very preferably all of the aforementioned properties in combination.

The most important function of the carrier material is to accommodate and carry the active substance and the envelope material. The aim in this context is to achieve high mechanical stability and a corresponding dispersibility of the microparticles in the end formulation.

Active ingredients that can be used are those having antibacterial and/or antimicrobial properties. Examples thereof are as follows:

bisbiguanides, bispyridines, pyrimidines, domiphen, benzalkonium and benzethonium, alkaloids, heavy metal ions such as zinc and copper, surface-active substances such as lauryl sulfate and lauryl sarcosinate and deoxycholate; triclosan, phenolic compounds such as eucalyptol, hexylresorcinol, menthol, methyl salicylate, phenol, 2-phenylphenol and thymol; antibiotics such as erythromycin, kanamycin, metronidazole, niddamycin, spyramycin and tetracycline, enzymes, such as amyloglycosidase, glucose oxidase and mutanase, salts of chlorhexidine.

As active ingredients it is additionally possible to use odorous substances such as menthol, peppermint oil, geranium oil and limonene, for example, or flavours such as menthol, peppermint oil, geraniol and limonene, for example.

The active ingredients may already be present in the composite particles of the invention, though it is also possible for the active ingredients to be present in a chemically bonded form and to be generated and/or released only after activation in the mouth. One example of this is the use of zinc alginate as envelope substance. Through ion exchange in the mouth, i.e. through contact with the saliva, the zinc ions are replaced by cations present in the saliva, such as sodium or potassium or calcium ions, or example. This has the effect not only of cancelling out the gellation of the zinc alginate, so dissolving the protective envelope, but also of releasing the zinc ions, which act as antimicrobial substances. Further examples are described in the text below.

Particularly preferred are active ingredients having a solubility of 20 to 300 g/l in organic solvents or water, or a melting point below 200° C.

The invention accordingly encompasses those composite particles in which at least one active ingredient is absorbed, but also those in which the active ingredient or ingredients is/are present in chemically bonded form, and those, too, in which there are both active ingredient(s) and chemically bonded active ingredient(s).

The composite particles of the invention comprise at least one envelope material. One effect of this envelope material is to control the release mechanism of the active ingredient.

Hence it is possible to use envelope materials which are degraded, and hence dissolved, by enzymatic reactions. Examples of these are polysaccharides which are cleaved by the alpha-amylase present in the oral cavity.

Other envelope materials, such as polyelectrolytes, are changed by pH change such either that they release the active ingredient or that they dissolve or become pervious to the active ingredient.

Another group of possible envelope materials do not dissolve, but instead allow the diffusion of the active ingredients through the envelope layer, with the consequence that the active ingredients are released in the oral cavity with a time delay. Examples thereof are hydrogels made of gelled alginate, pectin, amylopectin, glycogen, methylcellulose, ethylcellulose, shellac, stearic acid and other fatty acids, fatty alcohols, gelatine, and Eudragits.

With a fourth group, ion exchange occurs in the oral cavity, as for example after contact with the saliva. One example of this is zinc alginate. Through exchange of the zinc ions for cations such as sodium or calcium ions, the gelling of the alginate is dissolved, and zinc ions are released. These zinc ions themselves constitute an active ingredient. Alternatively, other active ingredients present in the composite particles may also escape from the composite particles following dissolution of the gel coat. In this case, then, two active ingredients, for example, or more, may be released simultaneously from the composite particles. Other examples of envelope substances which are activated by ion exchange are polystyrenesulfonate, zeolites or synthetic resins. Here it is possible to vary the active substance by means, for example, of a suitable choice of the cations and/or of the incorporated ions.

Also encompassed, finally, are envelope materials which release the active ingredient and/or become pervious to the active ingredient as a result of temperature change. Examples of these are meltable saturated fatty acids such as capric acid or lauric acid, lauryl alcohol, myristyl alcohol; unsaturated fatty acid such as elaidic acid, polyethylene glycol of low molar mass, or waxes, where approved.

Particularly preferred envelope materials may be applied from an aqueous solution to the carrier particles, but following application exhibit low solubility in water. This allows high storage stability and prevents the unwanted release of active ingredient very effectively. Furthermore, it becomes easy to produce the composites. Examples thereof are gelled polysaccharides.

Particularly preferred envelope materials are zinc alginate, amylase or hydroxymethylpropylcellulose.

As already indicated above, the present invention encompasses composite particles which comprise the carrier material and at least one envelope material, an active ingredient being released from the envelope material by activation in the oral cavity. Also encompassed, however, are embodiments in which the composite particles comprise the carrier material, at least one active ingredient and at least one envelope material which, through activation, releases additional active ingredient. In these cases the active ingredients may be the same or different. A feature of yet another embodiment is that the composite particles comprise the carrier material, at least one active ingredient and at least one envelope material which releases no additional active ingredient. Hybrid forms of the above embodiments are likewise encompassed. Thus, for example, it is also possible for the composite particles of the invention to comprise the carrier material, at least one active ingredient, at least one envelope material which releases additional active ingredient by activation, and at least one envelope material which releases no additional active ingredient.

Through the choice of the envelope materials and of the carrier material it is possible to control the release mechanism. Thus, for example, the choice of carrier material influences the rate at which the active ingredient can be dissolved out of the pores. The choice of envelope material likewise influences the release rate. Accordingly, for example, with selection of two envelope materials, the outermost layer of one envelope material releasing active ingredient through activation, and the underlying layer permitting diffusion-controlled release of a further active ingredient from the pores of the carrier, it is possible first to release the active ingredient quickly from the topmost envelope layer and after that, slowly, to release the active ingredient from the pores, by diffusion.

The composite particles of the invention preferably comprise at least one envelope material having mucoadhesive properties, boosting or enabling the attachment of the particles to the mucosa present in the mucous membrane of the mouth. This ensures that the particles of the invention remain in the oral cavity for a sufficiently long time and in sufficient quantity.

In one alternative embodiment there is no envelope material with mucoadhesive properties present. As a result of the low particle size, however, in this case as well the composite particles of the invention are able to seat themselves between the teeth and in small hollows and depressions in the oral cavity in such a way that they remain in the oral cavity for a sufficiently long time and in sufficient quantity.

Particular preference is given to using not only silicon dioxide carrier materials but also envelope materials which are approved for the cosmetic sector, advantageously for the food sector and the cosmetic sector.

From the possible combinations identified above, a number of possible structures emerge for the composite particles of the invention.

In one preferred embodiment the structure in question is that referred to as a core-shell structure, where the carrier material, optionally with envelope material and/or active ingredient drawn into the pores, forms the core, and this core is enveloped, as far as possible completely, by at least one envelope material (shell).

A second particularly preferred embodiment is notable for the fact that the active ingredient or active ingredients and the envelope substance or envelope substances are arranged in the pores of the porous $SiO_2$ carrier so extensively that, as demonstrated by XPS analysis of the outermost atomic layer of the product system, at least some, preferably at least 10%, more preferably at least 15%, very preferably at least 20%, of the outer surface of the product system is formed by the carrier material.

In this embodiment the composite particles of the invention have the advantage that they are mechanically very stable. Furthermore, through control of the pore structure of the carrier and also through selection of the active ingredient, it is possible to regulate the diffusion-controlled release of the active ingredient over a relatively long time.

In this second embodiment, furthermore, the composite particles of the invention have the advantage that they can be incorporated outstandingly into oral hygiene articles such as, for example, toothpaste. The inventors have in fact found that when a carrier material is selected which has been developed as an additive for toothpastes and optimized for that purpose, the composite particles of the invention can be incorporated to particularly good effect into oral hygiene articles. Without being tied to any particular theory, the inventors are of the view that the fact that the active ingredient and the envelope substance are present largely to exclusively in the pores of the carrier and that a large part of the outer surface of the additive continues to be formed by the carrier material means that the incorporation properties are such as if there were no active ingredient or no envelope substance present in the carrier. This can be explained by interactions occurring essentially only between the other components of the toothpaste formulations and the carrier material.

The envelope substances are lodged largely, in other words preferably to an extent of at least 30% by weight, more preferably 50% by weight, very preferably 70% by weight, based in each case on the amount of active ingredient used, into the pores of the carrier material impregnated with active ingredient beforehand. With particular preference there is no active ingredient on the surface of the particles in this embodiment. The additives of the invention are therefore preferably distinguished by the formation in the pores of an active ingredient layer, located closer to the core of the carrier material, and a protective layer, located towards the outer surface of the carrier material. The active ingredient is therefore shielded from influences from its surroundings. It is therefore preferred for there to be no active ingredient on the outer surface of the product systems of the invention, according to XPS measurement of the outermost atomic layer, or for a maximum of 10%, preferably a maximum of 5%, more preferably a maximum of 1% of the outer surface to be covered with active ingredient. This is advantageous in particular for specific applications in which the active ingredient fractions are not to trigger any premature, unwanted reaction and are not to exert any undesirable, harmful effect on humans, animals or plants. This can be ensured to particularly good effect in this second embodiment.

With regard to the mode of action of the protective system it can be assumed, as stated above in the description of the envelope substances, that the envelope substance seals the pores of the porous carrier which has been partially provided with active ingredient. Following partial dissolution or partial destruction of this seal of the pores, the active ingredient can be released. The protective system for the active ingredient/ingredients is preferably formed such that the protective system dissolves in accordance with one of the mechanisms defined above, thereby allowing the active ingredient to be released. It is also preferred, however, for the additives of the invention to have a protective system in the form of a matrix through which the active ingredient can diffuse and/or water can gain access to the active ingredient.

As a result of the fact that the protective system is largely or wholly lodged in the pores of the carrier material, the antimicrobial composites of the invention are externally dry powders, preferably free-flowing powders. This means that the free-flowability of the product as measured using the flow funnels of DIN 53492—see also description of measurement methods later on below—has a value of between 1 and 4, preferably between 1 and 3, more preferably between 1 and 2, and very preferably a value of 1. As a result, the additives of the invention have particularly good processing and transportation properties.

Irrespective of whether the composite particles of the invention have a core-shell structure or are configured in accordance with the second embodiment, it has proved to be advantageous if the weight ratio of protective system to active ingredient is in the range from 10:1 to 1:10. The ideal ratio depends on the chemical nature and the physicochemical properties of the active ingredient and of the carrier material, and also of the envelope substance, and can be determined for each combination of materials by means of simple series of experiments. A higher carrier material charge may mean that sufficient protective substance can no longer be introduced into the pores. Too low a charge is not economically rational. With particular preference the weight ratio of protective system to active ingredient is in the range from 10:1 to 1:10, very preferably in the range from 5:1 to 1:5 and more particularly preferably in the range from 2:1 to 1:3.

As well as the weight ratio it may be advantageous, depending on combination of materials, to observe a defined proportion between DBP absorption and amount of active ingredient absorbed. Without being tied to any particular theory, the inventors are of the view that DBP, the active ingredients to be absorbed, and the protective substances frequently have a similar space occupancy in the pores of the carrier material and also penetrate pores of similar size. Accordingly, this proportion provides information on how much space is still present in the pores that are accessible to the envelope material, and is therefore able to ensure that a sufficient amount of active ingredient and also protective substance can be introduced into the pores. Hence it has proved to be advantageous for the active ingredient charge of the porous carrier to be at least 10% to 90% by weight, preferably 10% to 80% by weight, more preferably 20% to 70% by weight and very preferably 30% to 60% by weight, based on the DBP absorption of the porous carrier. In one special embodiment the active ingredient charge of the porous carrier is 1% to 9% by weight, based on the DBP absorption of the porous carrier.

As already explained, it is an essential feature of the composite particles of the invention, in the second embodiment, that the greatest amount of the protective substance is present within the pores of the carrier material, and not absorbed on the surface of the carrier material. In this way it is possible to prevent the protective system becoming damaged, by abrasion, for example, and deactivated. For the same reason it has proved to be advantageous to specify the absorbed quantity of protective substance in relation to the DBP absorption of the carrier material. It has proved to be particularly advantageous for the envelope substance charge of the porous carrier to be at least 10% to 90% by weight, preferably 10% to 80% by weight, more preferably 20% to 70% by weight and very preferably 20% to 50% by weight, based on the DBP absorption of the porous carrier. If the charge is too low, then, depending on the pore structure of the carrier material, there may be a deterioration in the effect of the protective system. Too high a quantity of protective system may have adverse consequences for the targeted deactivation and/or is economically ineffective, since the aim is to accommodate the maximum amount of active ingredient and the minimum amount of protective substance.

Independently of whether the composite particles of the invention have a core-shell structure or are configured in accordance with the second embodiment, they may comprise one or more active ingredients, and the active ingredients may be present as a homogeneous mixture or in layer form within the porous carrier. In the case of the layer-form variant, there may be two, three or more layers present, which may differ in nature and composition of the active ingredients.

The composite particles of the invention can be produced by contacting at least one porous amorphous silicon dioxide with at least one envelope substance or with at least one active ingredient and at least one envelope substance.

In the cases in which the composite particles of the invention comprise an active ingredient, application thereof may take place as follows:

In the case of liquid active ingredients, the active ingredient may be drawn directly into the carrier material. For this purpose, the carrier material can be placed in a suitable mixer and the active ingredient can be added by metering, dropping, spraying, etc. Corresponding technologies are known to the skilled person.

In the case of non-liquid active ingredients, they may be dispersed in a dispersion medium or dissolved in a solvent. The carrier material is then contacted with the solution or dispersion, by immersion, for example, or the solution or dispersion is sprayed on, and hence the active ingredient together with the solvent or dispersion medium is drawn into the pores of the carrier. The solvent or dispersion medium is subsequently removed, by evaporation, for example.

In one variant of the method of the invention the active ingredient itself is actually produced within the carrier material. This can be done by causing one or more precursors of the active ingredient to be drawn into the carrier material, and then generating the active ingredient by chemical reaction or physical exposure. Physical exposure may be, for example, a heat treatment at high temperature (calcining).

One example of a chemical synthesis of active ingredient within the carrier is the charging of the carrier with sodium alginate and subsequently with a ZnCl solution, thus forming zinc alginate as active substance in the pores of the carrier.

Another way of absorbing non-liquid active ingredients into the carrier material is to melt the active ingredient, so that the carrier material draws up the melted active ingredient. This way, however, works only for active ingredients which can be melted without decomposition.

As already observed, it is particularly preferred for the composite particles of the invention not to have any active ingredient on their outer surface. By outer surface is meant the surface which is not formed by pores or other cavities in the interior of the carrier particles. This can be achieved by washing the charged particles with a solvent in which the active ingredient is soluble. The washing operation must be controlled such that it is quick enough for substantially only the active ingredient adhering to the surface of the particles to be washed off, and not the active ingredient which has been drawn into the pores. Since the release of active ingredient from the pores is diffusion-controlled, i.e. controlled by a slow process, only a little active ingredient is leached from the pores in a rapid wash. Alternatively, active ingredient adhering to the surface of the carrier particles may also be inhibited. This can be done, for example, through chemical reaction with a suitable agent.

The active ingredients defined above can be used in the method of the invention.

The composite particles of the invention comprise at least one envelope material, said envelope material/envelope materials I) being applied as a shell or multi-layer shell on the carrier which optionally carries a charge of active ingredient, or II) being applied partly in the pores and partly as a shell or multi-layer shell on the carrier which optionally carries a charge of active ingredient, or III) being substantially accommodated in the pores of the carrier, which optionally carries a charge of active ingredient, in such a way that, as demonstrated by XPS analysis of the outermost atomic layer of the product system, at least some, preferably at least 10%, more preferably at least 15%, very preferably at least 20%, of the outer surface of the composite particles is formed by the carrier material.

In cases I) and II), the charge of active ingredient(s) is first of all produced as described above. In the case of method I), the pores can be filled completely with active ingredient(s); in the case of method II), at least some of the volume of the pores must remain free for the envelope material.

Where an envelope material is used which comprises a chemically bonded active ingredient, i.e. an envelope material which, following activation in the oral chamber, is able to release an active ingredient, there is no need for the prior charging with a further active ingredient. In this case it may be that the pores are completely filled with this envelope material, and carrier particles thus filled are enveloped with a shell of the same or a different envelope material.

In method variants I) and II), the envelope material/materials are preferably applied such that the particles are largely completely, preferably completely, encapsulated with the envelope material. This may be accomplished, for example, as follows:

a) introducing at least one carrier material in a solids mixing unit
b) optionally evacuating the solids mixing unit
c) optionally preimpregnating the carrier material with at least one envelope material up to a maximum of 50% by weight of the absorption value (corresponding to the DBP number)
d) optionally adding at least one active ingredient in the solids mixing unit
e) optionally impregnating the carrier with active ingredient
f) optionally inhibiting the active ingredient adhering to the outer particle surface of the carrier material, and/or washing and/or drying
g) adding at least one envelope material
h) impregnating the carrier with at least one envelope material until the material can no longer be absorbed by the particles and there is a change in the flowability of the powder
i) optionally washing and/or drying
j) optionally reactively inhibiting the active ingredient adhering to the outer particle surface of the carrier material, and/or washing and/or drying.

In the case of method III), the method of the invention preferably comprises the following steps:

a) introducing at least one carrier material in a solids mixing unit
b) optionally evacuating the solids mixing unit
c) optionally preimpregnating the carrier material with at least one envelope material up to a maximum of 50% by weight of the absorption value (corresponding to the DBP number)
d) optionally adding at least one active ingredient in the solids mixing unit
e) optionally impregnating the carrier with active ingredient
f) optionally inhibiting the active ingredient adhering to the outer particle surface of the carrier material, and/or washing and/or drying
g) adding at least one envelope material
h) impregnating the carrier with at least one envelope material i) optionally washing and/or drying
j) optionally reactively inhibiting the active ingredient adhering to the outer particle surface of the carrier material, and/or washing and/or drying.

Examples of solids mixing units which can be used in step a) include the following: kneaders, paddle dryers, tumble mixers, vertical mixers, paddle mixers, Schugi mixers, cement mixers, Gericke continuous mixers, Eirich mixers and/or silomixers. The temperature in the mixing unit, depending on the protective system and on the active ingredient, is preferably between 5° C. and 250° C.

Step b) is optional, i.e. need not necessarily be carried out. By evacuating the solids mixing unit following addition of the carrier material, however, it is possible to evacuate the pores of the carrier material and to extract gas or air contained therein, thereby allowing a more complete charging of the carrier material with active ingredient(s) and envelope material(s) to be achieved.

Step c) is optional and is carried out depending on the existing pore structure of the carrier material. For the efficiency of the protective system of the invention it is necessary for the pores as far as possible completely to be sealed outwardly with envelope material, so that the active ingredient is protected from contact with solvents. In the majority of porous carrier materials, the pores communicate with one another in a more or less complex system. As a result it is possible for narrow pores in the interior of the carrier material, into which neither active ingredient nor protective substance is able to penetrate, owing for example to the viscosity, to communicate with a pore into which the active ingredient has penetrated. In this way it would be possible for the active ingredient, although not being able to be dissolved out of the actual pore into which it has been drawn, to nevertheless come into contact in the interior of the carrier with solvent, through the smaller "secondary pore", and hence to be dissolved out to some extent nevertheless. By preimpregnation of the carrier material with the envelope material it is possible to prevent such unwanted effects, since "side channels" can be sealed off by this means before the active ingredient is absorbed. In particularly preferred embodiments, protective substance is introduced in the form of a solution or as a melt.

In step d), optionally, i.e. in those cases which the composite particles contain at least one active ingredient not released from the envelope material, the active ingredient, or two or more active ingredients, is or are added to the solids mixing unit. If two or more active ingredients are to be added, they may be added simultaneously or in succession. Where they are liquid, the active ingredients can be added directly or as a melt, or else as a solution or in the form of a dispersion or suspension. Active ingredients which can be used are all of the active ingredients described in greater detail above.

In step e), optionally, i.e. in those cases in which the composite particles contain at least one active ingredient which is not released from the envelope material, the active ingredient/ingredients is or are introduced into/onto the carrier material and/or the preimpregnated carrier material. In this case the mixing time/incorporation time is made such as to ensure maximum penetration of the active ingredients into the pores, or complete adhesion. Impregnation with an active ingredient is at an end when the free-flowability of the product as measured with the flow funnels in accordance with DIN 53492—see also description of measurement methods later on below—has a value of between 1 and 4, preferably between 1 and 3, more preferably between 1 and 2, and very preferably a value of 1. In one particularly preferred embodiment the active ingredient is dissolved in a solvent, the solution is brought into/onto the support, and the resulting product is dried in order to remove the solvent.

In method variant I), the pores may be completely filled with active ingredient, since the particles are largely completely, preferably completely, enveloped with the envelope material.

In one specific method variant III) of the present invention, the active ingredients and also the protective system are largely or completely embedded in the pores of the carrier material, and so parts of the outer surface of the carrier material are bare. In this case the pores may not be completely filled with active ingredient.

Since, during impregnation in step e), i.e. during the drawing of the active ingredient into the pores, it is generally not possible to prevent at least a few molecules of active ingredient adhering to the outer surface of the carrier, it can be sensible to inhibit these active ingredient molecules in an optional step f) or to remove them from the outer surface of the carrier, by washing, in order to ensure that active ingredient is in fact present only in the pores. In the case of inhibition, active ingredient lying on the surface is reacted by means of a corresponding reactant to form a non-reactive substance. In the case of washing, the active ingredient is washed off by means of suitable solvent. Depending on active ingredient, two or more washing operations are necessary. Where the active ingredient/ingredients has/have been added in the form of a solution or suspension, the solvent is preferably removed before the protective substance is added, preferably by means of evacuation or baking.

In step g), the envelope material, or two or more envelope materials, is or are added to the solids mixing unit. If two or more envelope materials are to be added, they may be added simultaneously or in succession. Where they are liquid, the envelope materials may be added directly or as a melt or else as a solution or in the form of a dispersion or a suspension. In one particularly preferred embodiment the envelope material is introduced in the form of a solution or as a melt.

In method variants I) and II), the amount of envelope material added and the mixing time are sufficient to ensure that the particles are largely completely, preferably completely, enveloped with the envelope material, i.e., that a core-shell structure has formed.

In method variant III), in which the envelope material is located largely in the pores, it must be ensured in step h) that the pores are filled as far as possible completely, since the pores that lead from the surface to the core of the carrier particle communicate with one another through inter-pore channels, which transmit solvent and could therefore result in the release of the active ingredient. Where the envelope material/envelope materials has/have been added in the form of a solution or suspension, it is preferred to remove the solvent by evacuation or baking.

In order to remove excess envelope materials, especially in method variant c), it is possible, if necessary, for a washing step with subsequent drying to take place in step i).

Depending on the active ingredient and protective system it may be sensible, instead of the inhibition and/or washing-off of the active ingredient adhering to the outer surface of the carrier, in step f), to carry out this inhibition and/or this washing operation following application of the protective layer, i.e. in step j). In general it will be more effective to carry out the washing and/or inhibition in step j) rather than in step f), since in step g) the pores have been sealed by the envelope material and hence in step j) only the molecules of active ingredient that are adhering to the outer surface are eliminated. It is also possible to carry out washing and/or inhibition both in step f) and in step j). It is also possible to carry out washing and inhibition in step f) and/or j).

In special cases, stages b) to e) and/or g) to h) are carried out repeatedly, and, in the case of repetition of steps d) and e) and/or g) and h), identical or different active materials and/or envelope materials may be used in each case. It is advantageous, furthermore, to select the envelope material and/or the active ingredient in steps c), d), e), g) and h), and also the mixing conditions, such that the active ingredient and/or envelope material always remains liquid and does not dry out or crystallize out on the surface of the particles.

In one particular embodiment of the method of the invention, step d) is carried out not after but rather before step a), i.e., the carrier material and the active ingredient/ingredients are mixed before being introduced into the solids mixing unit. Particular advantages in this case lie in the uniformity of the distribution of active ingredient in the carrier particles. This is very important in the case of a high active ingredient charge, in order subsequently to be able to charge all particles uniformly with the protective system.

In principle it is also possible to carry out steps c) and d) simultaneously and to add a mixture of at least one active ingredient and at least one protective substance. This may be particularly sensible when the protective substance is able to penetrate into smaller pores than the active ingredient and hence it is possible for the effect described above to occur, i.e. the "sealing" of side pores, even when introduction of protective substance and active ingredient is simultaneous.

In order to provide optimum assurance of the best possible functionality of the composite particles of the invention, more particularly the mechanical stability, care should be taken to ensure that, on the one hand, there is no active ingredient on the carrier surface, and on the other hand that there is also, as far as possible, no protective substance present on the outer surface of the carrier. Both components ought ideally to have been drawn completely into the pores of the carrier material. In order for this to be achieved, the amount of envelope substance/substances added in step g) ought, in method variant III), to be regulated such that the total amount of active ingredient/ingredients plus envelope substance/substances added during the production of the product systems corresponds to 50% to 100% of the DBP absorption value (in accordance with DIN 53601) of the carrier material.

Alternatively, however, the production operation may also be controlled by the pore volume; in that case, preferably, the amount of protective substance/substances added in step g) is regulated such that the total amount of active ingredient/ingredients and envelope substance/substances is greater than the total pore volume of the carrier material, and that the excess envelope substance/substances is absorbed by addition of carrier material and/or of carrier material charged with active ingredient/ingredients.

The mixing intensities and the metering in the method of the invention ought to be harmonized with one another such that in method variant III) the free-flowability at the end of the application process is ensured, i.e. that at every point in time there is a free-flowable powder present in the mixer.

This makes it possible to ensure that the protective substance and/or active ingredient is taken up fully into the pores and does not adhere to the outer surface of the carrier. If metering takes place too quickly or if mixing takes place at too low an intensity, the charging of the particles may lack uniformity, and ultimately this may result in the pores of some particles being filled completely with active ingredient, with no possibility any longer for protective substance to penetrate. Details of this method may be found in DE102008000290. The content of said patent application is hereby adopted explicitly into the content of the present specification. In method variants I and II, more envelope substance may be added, and/or envelope substance may be added for longer, accordingly, to ensure that a core-shell structure is formed, the formation of such a structure possibly being apparent, for example, from a change in the flow behaviour of the mixture.

Conventional methods in which a large amount of active substance is added rapidly to the carrier material have the disadvantage that there may be gas inclusions in the pores, i.e. that the pores are filled not, as desired, with active ingredient, but rather with gas.

In connection with the choice of the mixing assembly, attention should also be paid to ensuring that the stirring elements, e.g. IKA Duplex mixing element in the H60 recording extruder or Somakon MP, are selected such that shearing stress produces very little or no abrasion. The test for abrasion on the particles is carried out by measuring the particle size distribution. For this purpose, in the mixing unit used subsequently, the carrier materials are introduced and the mixing operation is commenced in accordance with the subsequent procedure. After a defined mixing time, samples are taken and their particle size distribution is ascertained. In the particle size distribution, the deviation from the $d_{50}$ value of the initial sample ought to be not greater than 5%. If, for example, the result of the particle size distribution prior to mixing is as follows:

Average particle size $d_{50}=23.72$ μm
and the result of the particle size distribution after mixing is as follows:

Average particle size $d_{50}=22.74$ μm
then this condition is met.

Independently of the method variants I) to III), it may be necessary for some envelope materials to carry out a gelling step in order to harden the envelope material. Thus, for example, the envelope material may be a polysaccharide, which following application is gelled by addition of $Zn^{2+}$ or $Ca^{2+}$. These techniques are known in principle, and a skilled person is therefore capable of appropriately modifying or supplementing the methods described above.

The composite particles of the invention can be used for producing oral hygiene articles such as, for example, toothpastes, mouth rinses and mouth sprays. These oral hygiene articles generally contain 5% to 15% by weight of the composite particles of the invention.

Measurement Methods
XPS Analysis of the Surface Composition

An important characteristic of the composite particles described lies in the maintenance of the silica particle surface. The active ingredient and the envelope substance are located only in the pore system, and so the surface of the particle continues to be composed of $SiO_2$ groups. This feature is critical in order that, through the use of these composite particles, the original processing properties and compatibilities with various coating formulations remain unaffected. The pure, clean silica particle surface is detected by means of X-ray-induced photoelectron spectroscopy (XPS). This allows surface-sensitive detection of the elemental composition, and also an analysis of the binding conditions.

Measurement Principle

One surface of the material is bombarded under ultra-high-vacuum conditions with soft X-radiation (e.g. MgKα, AlKα). This removes what are called photoelectrons, whose kinetic energy after leaving the surface of the material is analyzed using an electron spectrometer (FIG. 1).

Where the sample measured is a metallic sample which is in electrically conducting contact with the spectrometer, the kinetic energy of the photoelectrons removed is given by:

$$E_{kin} = h\nu - E_B - \Phi_{Sp}'$$

i.e. the energy of the irradiated X-radiation (hv) minus the binding energy ($E_B$) minus the work function of the spectrometer ($\Phi_{Sp}'$). In the case of electrically non-conducting materials there are also contributions to be taken into account. From this relationship between the excitation energy and the measured kinetic energy, therefore, it is possible to determine the binding energy of the electrons to the sample atoms. This energy is directly dependent on the chemical binding state of the elements. For example, therefore, for metallic platinum on a carrier, the value measured is different from that for divalent or tetravalent platinum. Sulphate sulphur yields values different from those for sulphide sulphur or sulphane sulphur, and PMMA yields different oxygen and carbon signals than polycarbonate, polyoxymethylene or Teflon.

Figure 2:
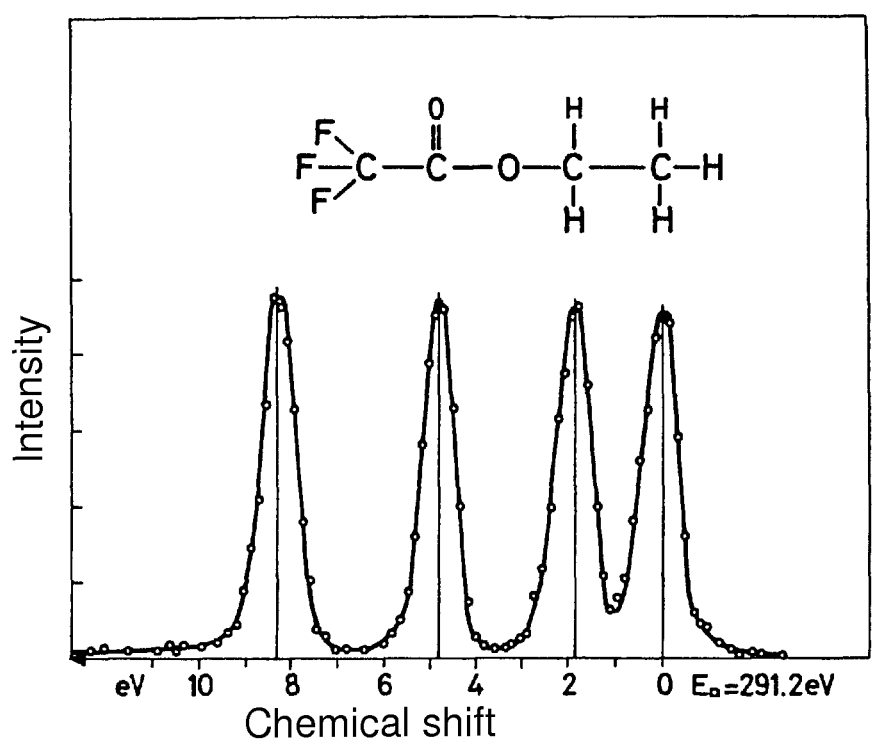
FIG. 2 depicts the XPS/ESCA spectrum for trifluoroacetic acid.

A classic example of an XPS result is given in FIG. 2. It is apparent that even different binding states of the carbon in ethyl trifluoroacetate can be identified on the basis of the "chemical shift" of the C signals. From the "chemical shift" of the XPS signals it is possible, therefore, to differentiate differently bonded atoms from one another, as a result of which it is possible to determine the magnitude of the fraction of the carrier and/or active-ingredient and/or protective-substance atoms on the surface of the oral-hygiene additives of the invention. In view of the possibility of being able to differentiate differently bonded atoms from one another, K. Siegbahn coined the name "ESCA" for this measurement technique (electron spectroscopy for chemical analysis), since chemical information is supplied. XPS spectra allow determination of which elements are present at which concentration in the region of the topmost atomic layers of materials, and the "chemical shift" of the XPS signals allows determination of the chemical binding state in which they exist.

By means of EDP-assisted evaluation methods it is possible to quantify this with high reproducibility. The values determined in this context typically correspond to a figure in area percent.

Using overview surface analyses, for example, it is possible to capture, for example, 0.5 cm² of a surface integrally, although the depth of penetration of the analysis is confined to the uppermost atomic layers. In this way, any microinhomogeneities present are averaged out.

The measurement of the photoelectrons emitted from the sample, as in the case of the XPS/ESCA technique, detects exclusively the region of the uppermost atomic layers, since the average free path length of these electrons is just a few atomic layers. Electrons which are released by ionization processes in deeper layers are no longer able to reach the surface and hence are unable to leave the sample. Consequently, the XPS technique using soft X-ray excitation radiation and measuring the low-energy photoelectrons removed as a result is automatically surface-specific and is focused on the surface properties of materials.

A further advantage of XPS is that, apart from hydrogen and helium, even light elements such as B, C, N and O can be detected quantitatively and a direct observation made of their chemical binding states.

Figure 3:
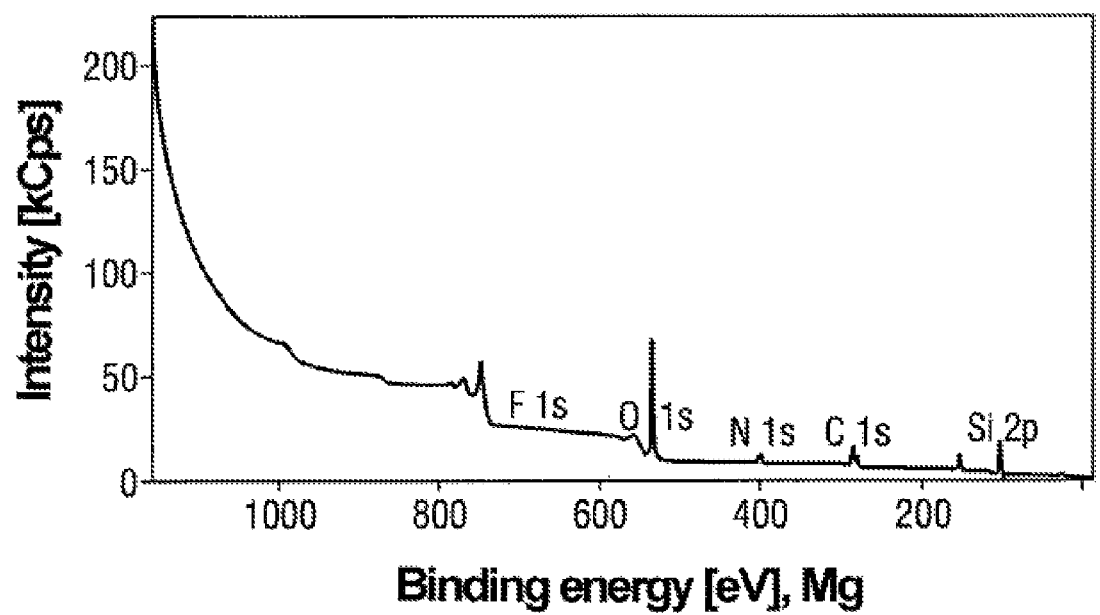
FIG. 3 depicts an XPS overview spectrum of Sipernat® 50 charged with 20% by weight 2-Mi, produced by the process of the invention.

FIG. 3 shows, as a general demonstration of the functioning of the XPS method, an XPS overview spectrum of Sipernat® 50 charged with 20% by weight of 2-Mi by the method of the invention in accordance with claim 15. It can clearly be seen which part of the surface is formed by $SiO_2$ and which by 2-Mi (which is not an active ingredient of the invention, but instead is only a demonstration substance for the purpose of illustrating the XPS method). By background subtraction and the use of the relative sensitivity factors of the elements, standardized methods can be employed to determine, from these data, quantitative information relating to the surface composition.

Procedure for XPS Measurements

The XPS measurements are carried out on powder beds, with integral detection of 0.5 square centimeter in each case. In order to prevent sample contamination and measurement artefacts, the samples are placed in a gold-coated, ultrapure-tantalum sample container (Alfa, 99.98%, approximately 0.25 mm in thickness, approximately 1.5 to 2 cm in size) in such a way that there is no caking, clinging or compaction of the samples. The amount of sample is chosen such that the holder is largely filled and such that at least an area of 0.5 square centimeter can be measured. Each sample is then transferred to a preliminary chamber of the XPS spectrometer (Leybold LHS12 or Leybold MAX 100 XPS system) and the chamber is evacuated to $10^{-8}$ mbar at room temperature for approximately 2 hours. After that, the sample under analysis is transferred into the main chamber of the XPS spectrometer, and the vacuum is increased to $4\times10^{-10}$ mbar in order to prevent impurities and measurement artefacts caused by possible hydrocarbon contamination or cross-contamination. The purity of the vacuum and of the residual gas in the measuring chamber of the XPS spectrometer is monitored continuously by means of a residual gas mass spectrometer (Quadrex 200, Inficon).

The XPS measurements are carried out by the ESCA method, using MgKα radiation, with an energy of 150 W. The electron energy analyzer (Leybold EA200) is operated with a pass energy of 72 eV in "fixed analyzer transmission" (FAT) mode. The reference used for the binding energy scale of the spectrometer was the $Au_4f_{7/2}$ signal of the SCAA83 standard from the National Physical Laboratory (NPL, Teddington, UK) at 84 eV, which is measured before and after the measurement of the sample under analysis. The electrostatic charging of the samples under analysis is compensated by low-energy electrons from an electron source of controlled incandescence which is mounted in the vicinity of the sample holder. This emission source, in turn, is shielded and insulated thermally, in order to prevent direct heat transfer to the sample under analysis.

Evaluation is carried out in accordance with the general recommendations of DIN technical report 39 and National Physical Laboratory Report DMAA(A)97, Teddington, UK, January 1987, and the existing knowledge of the working committee on "surface and microregion analyses" NMP816 (DIN). A DS 100 data set is utilized in order to evaluate the XPS data by means of standard routines (with subtraction of the X-ray satellites and of the background, and with account taken of the relative sensitivity factors valid for the spectrometer used (and stored in the data system of the spectrometer) for the electron level indicated in each case). All figures are given in area percent.

Analysis of the Physicochemical Properties of the Carrier Material

Determination of the DBP Number:

The DBP absorption (DBP number), which is a measure of the absorbency of a porous carrier material, is determined in a method based on standard DIN 53601, as follows:

12.50 g of carrier material in powder or bead form and with a moisture content of 0%-10% (the moisture content is adjusted if necessary by drying in a drying cabinet at 105° C.) are introduced into the kneader chamber (article number 279061) of the Brabender Absorptometer "E" (without damping of the outlet filter of the torque transducer). In the case of granules, the sieve fraction from 3.15 to 1 mm (stainless steel sieves from Retsch) is used (by gentle pressing of the granules through the sieve with a pore size of 3.15 mm using a plastic spatula). With continuous mixing (kneader panels rotating at a speed of 125 rpm), dibutyl phthalate is added dropwise at room temperature to the mixture at a rate of 4 ml/min using the Brabender T 90/50 Dosiomat. Its incorporation by mixing takes place with only a small amount of force, and is monitored by means of the digital display. Towards the end of the determination the mixture becomes pasty, which is indicated by a sharp increase in the required force. When the display shows 600 digits (torque of 0.6 Nm), an electrical contact shuts off both the kneader and the DBP feed. The synchronous motor for the DBP feed is coupled to a digital counter, and so the consumption of DBP in ml can be read off.

The DBP absorption is reported in the unit [g/(100 g)] with no decimal places. and is calculated using the following formula:

$$DBP = \frac{V * D * 100}{E} * \frac{g}{100\ g} + C$$

where DBP=DBP absorption in g/(100 g)
V=consumption of DBP in ml
D=density of DBP in g/ml (1.047 g/ml at 20° C.)
E=initial mass of silica in g
C=correction value from moisture correction table, in g/(100 g)

The DBP absorption is defined for anhydrous, dried carrier materials. When moist carrier materials are used, especially precipitated silicas or silica gels, it is necessary to factor in the correction value C for the calculation of the DBP absorption. This value can be ascertained from the correction table below; for example, a water content in the carrier material of 5.8% would imply an add-on of 33 g/(100 g) for the DBP absorption. The moisture content of the carrier material is determined in accordance with the method described below for "Determination of the moisture content or loss on drying".

TABLE 1

Moisture correction table for dibutyl phthalate absorption - anhydrous -

| % moisture content | .0 | .2 | .4 | .6 | .8 |
|---|---|---|---|---|---|
| 0 | 0 | 2 | 4 | 5 | 7 |
| 1 | 9 | 10 | 12 | 13 | 15 |
| 2 | 16 | 18 | 19 | 20 | 22 |
| 3 | 23 | 24 | 26 | 27 | 28 |
| 4 | 28 | 29 | 29 | 30 | 31 |
| 5 | 31 | 32 | 32 | 33 | 33 |
| 6 | 34 | 34 | 35 | 35 | 36 |
| 7 | 36 | 37 | 38 | 38 | 39 |
| 8 | 39 | 40 | 40 | 41 | 41 |
| 9 | 42 | 43 | 43 | 44 | 44 |
| 10 | 45 | 45 | 46 | 46 | 47 |

Determination of the Moisture Content or Loss on Drying

The moisture content or loss on drying (LoD) of carrier materials is determined in a method based on ISO 787-2 after 2-hour drying at 105° C. This loss on drying is composed predominantly of water moisture.

Procedure 10 g of the carrier material in powder, bead or granule form is weighed out to an accuracy of 0.1 mg (initial mass E) into a dry glass weighing boat with ground-glass lid (diameter 8 cm, height 3 cm). With the lid open, the sample is dried in a drying oven at 105±2° C. for 2 h. Thereafter the weighing boat is closed and is cooled to room temperature in a desiccator cabinet with silica gel as drying agent.

The weighing boat/glass beaker is weighed to an accuracy of 0.1 mg on a precision balance, in order to determine the final mass A. The moisture content (LoD) in percent is determined in accordance with $$LoD=(1-A/E)*100,$$

where A=final mass in g and E=initial mass in g.
Average Particle Size $d_{50}$

The particle distribution of the product systems of the invention is determined by the principle of laser diffraction on a laser diffractometer (Horiba, LA-920).

The particle size of powders is determined by preparing a dispersion having a weight fraction of approximately 1% by weight $SiO_2$, by stirring the powder into water.

Immediately after the dispersing operation, the particle size distribution of a sample of the dispersion is determined using the laser diffractometer (Horiba LA-920). The relative refractive index to be selected for the measurement is 1.09. All measurements are made at room temperature. The particle size distribution and also the relevant variables, such as the average particle size $d_{50}$, are calculated automatically by the instrument and displayed as a graph. Note should be taken of the indications in the operating instructions.

Determination of the BET Surface Area

The specific nitrogen surface area (referred to below as BET surface area) of the silica in powder form, containing approximately spherical particles, or granular, is determined in a method based on ISO 5794-1/Annex D using the TRISTAR 3000 instrument (from Micromeritics) and the multipoint determination of DIN-ISO 9277.

Determination of the Total Pore Volume

The total pore volume is determined by means of mercury porosymmetry. The method is based on the Hg intrusion of DIN 66133 (with a surface tension of 480 mN/m and a contact angle of 140°), using an Autopore IV 9500 instrument from Micromeritics.

Prior to the measurement, the silica is subjected to a pressure treatment. This is carried out using a manual hydraulic press (order No. 15011 from Specac Ltd., River House, 97 Cray Avenue, Orpington, Kent BR5 4HE, UK). 250 mg of silica are weighed into a pellet die with an internal diameter of 13 mm, from Specac Ltd., and loaded with 1 t according to the display. This load is maintained for 5 s and readjusted if necessary. Thereafter the sample is decompressed and dried in a forced-air drying cabinet at 105±2° C. for 4 h.

The silica is weighed out to an accuracy of 0.001 g into the type 10 penetrometer and, for effective reproducibility of the measurement, the initial mass is selected such that the "stem volume used", in other words the percentage volume of Hg consumed to fill the penetrometer, is 20% to 40%. The penetrometer is subsequently evacuated slowly to 50 µm Hg and left at that pressure for 5 min.

The Autopore instrument is operated according to the operating instructions with the software version IV 1.05. Each measurement is corrected by a blank measurement of the penetrometer. The measurement range is 0.0042-414 MPa.

Determination of the Free-flowability

The free-flowability is assessed using glass flow vessels with different outflow diameters. Evaluation takes place using ratings 1-7 (see Table 2). The figure reported is the measurement vessel from which the powder still just flows without coming to a halt.

TABLE 2

| Vessel No. | Outflow width [mm] | Evaluation while powder flow is still smooth |
|---|---|---|
| 1 | 2.5 | Very good |
| 2 | 5 | ↑ |
| 3 | 8 | | |
| 4 | 12 | | |
| 5 | 18 | | |
| 6 | 24 | | |
| 7 |  | Inadequate (does not run through No. 6) |

The examples which follow serve to illustrate the present invention, but without restricting it in any way.

EXAMPLE 1

40 ml of a 1.5% strength by weight sodium alginate solution are added with continuous stirring in a Somakon laboratory mixer to 20 g of SIPERNAT® 50 S. The resulting free-flowing powder is introduced into 500 ml of a 1% strength by weight $ZnCl_2$ solution and stirred therein using a magnetic stirrer for 1 hour. The particles are filtered and dried at 60° for two days. The zinc ion concentration is then 1% by weight, based on the total mass of the particles. If the zinc ion concentration is to be increased, then the charging procedure described can be repeated.

EXAMPLE 2

In this example, the carrier materials are loaded with an active ingredient and additionally with an envelope material that releases a further active ingredient. 20 g of SIPERNAT® 50S are charged to a Somakon laboratory mixer. The double-walled mixing unit is heated to 50° C. and 10% by weight of crystalline menthol is added to the $SiO_2$ powder. While the menthol melts and penetrates the pores, stirring takes place continuously at approximately 200 rpm. Thereafter the mixing apparatus is slowly cooled, and the menthol solidifies in the pores.

This active ingredient is subsequently encapsulated by the method described in Example 1, in which it must be ensured that the maximum accommodation capacity of the particles is not exceeded, in order that the powder remains free-flowing at all times. The particles gelled in $ZnCl_2$ are dried in a vacuum drying cabinet at 35° C. for 3 days.

EXAMPLE 3

Figure 4:
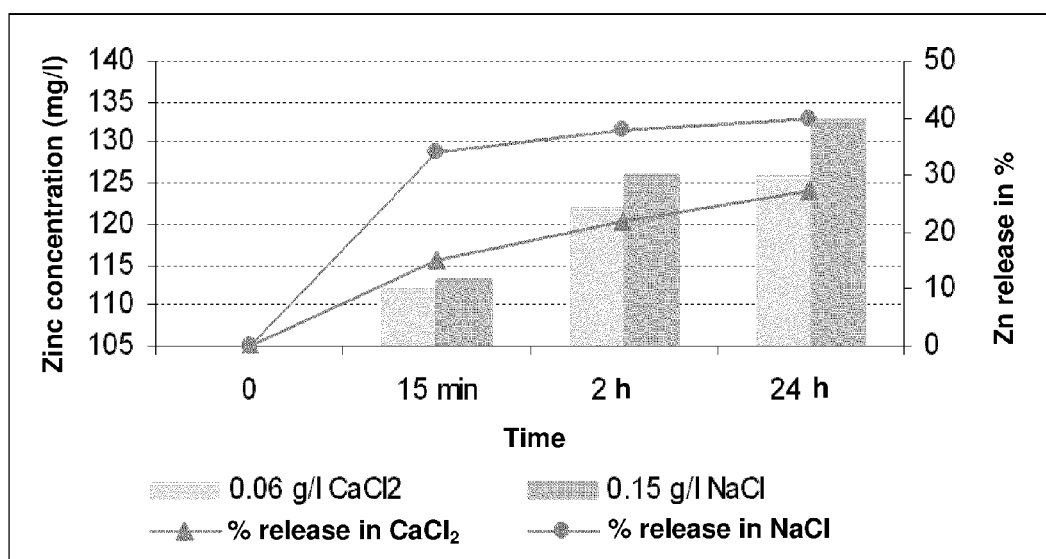
FIG. 4 depicts a time profile of ion-exchange-initiated release of zinc from the zinc alginate in a $CaCl_2$ or NaCl solution.

Of the charged Sipernat described in Example 1, 5 g are taken off and are dispersed in 100 ml of a 0.06 g/l $CaCl_2$ solution or in 100 ml of a 0.15 g/l NaCl solution. The results for delayed release are illustrated in FIG. 4. It is seen that, even after 24 hours, active ingredient is still released and hence the long-term effect is ensured.

EXAMPLE 4

Figure 5:
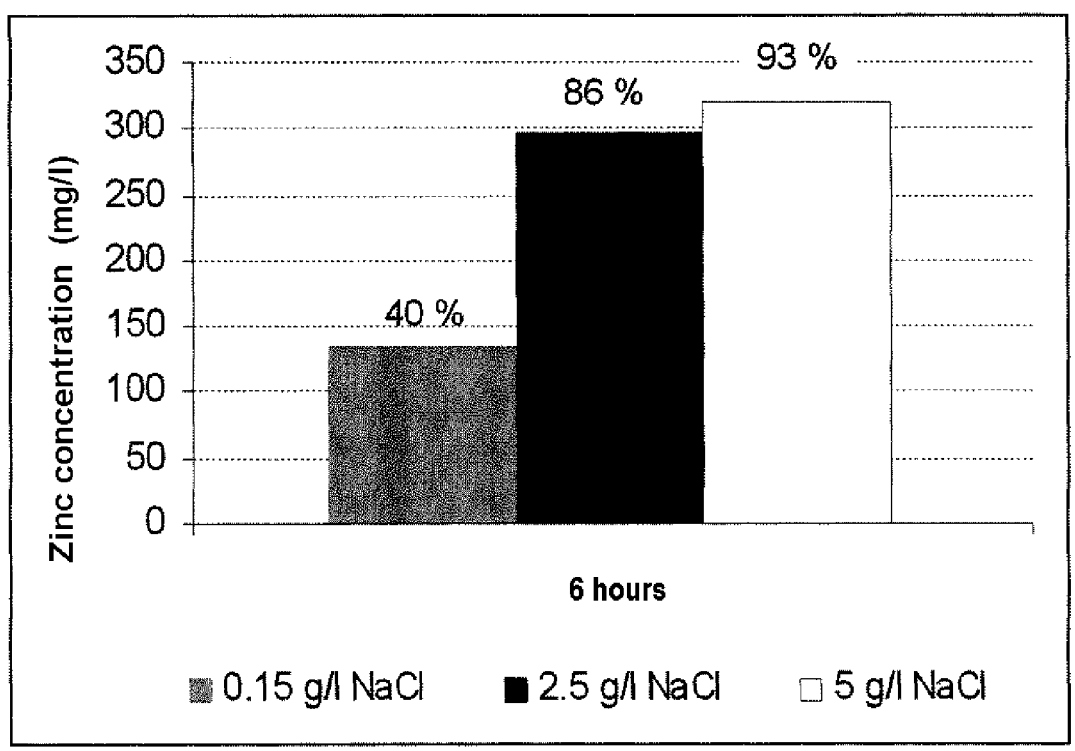
FIG. 5 depicts the effect of counterion concentration in the ion-exchange-initiated release of zinc from the zinc alginate of the composite particles of the invention after 6 hours.

Of the charged Sipernat described in Example 1, 5 g are taken off and are dispersed in 100 ml of a 0.15 g/l, 2.5 g/l or 5 g/l NaCl solution. The results for the effect of the counterion concentration are illustrated in FIG. 5. This shows that the release time and rate can also be influenced by modifying the counterion concentration, as for example by further additions to the oral care products.

EXAMPLE 5

Figure 6:
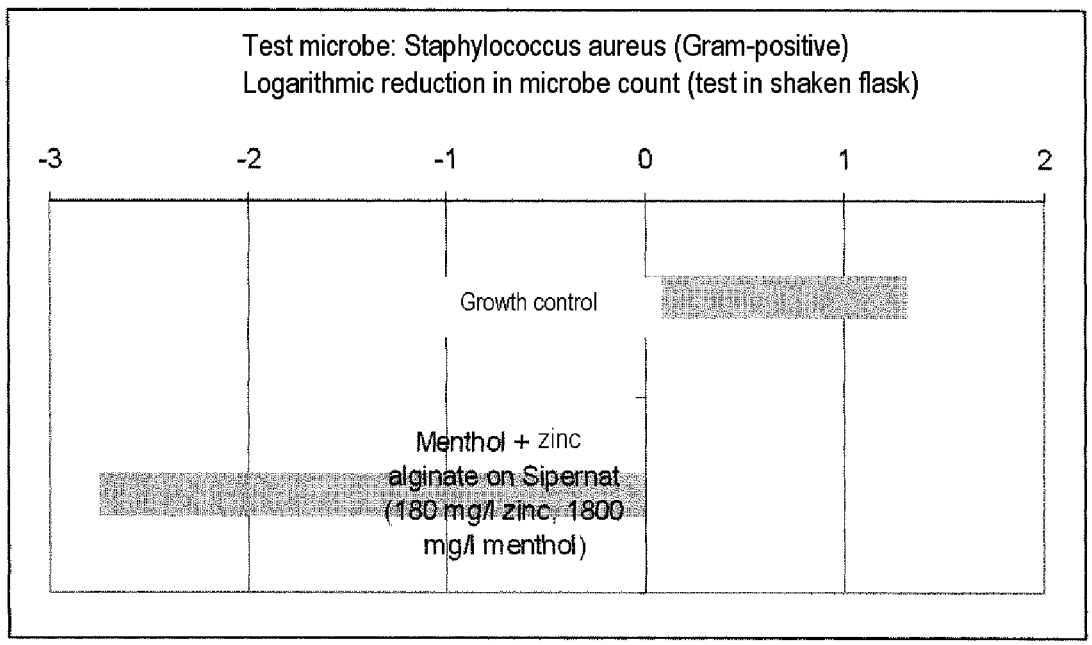
FIG. 6 depicts the activity of the composite particles of the invention on Staphylococcus aureus.

Of the specimens produced in Example 2, 300 mg are taken and are used for antibacterial tests in 50 ml shaken flasks. The microorganism selected was the standard test microbe *Staphylococcus aureus*, and the antibacterial effect of the composite on the bacterium was documented. The result of the test is set out in FIG. 6. It is apparent that exposure to the composite particles of the invention killed more than 99% of the microbes.

The invention claimed is:

1. Composite particles as additives for toothpaste and mouthwash, wherein the particles comprise
    a porous carrier of amorphous $SiO_2$, having an average particle size of 3 to 50 pm, and a specific surface area of between 50 and 550 $m^2/g$,
    at least one active ingredient, or a combination thereof
    and at least one envelope material, wherein the at least one envelope material releases an active ingredient following activation in the oral chamber,
    wherein the weight ratio of the envelope material or the sum of the envelope materials to the active ingredient or the sum of the active ingredients is in the range from 10:1 to 1:10,
    wherein at least one envelope material is selected such that the active ingredient is released in the oral cavity by diffusion, pH change, enzymatic degradation of the envelope material, temperature change, ion exchange or dissolution of the envelope material
    and wherein, as demonstrated by XPS analysis of the outermost atomic layers of the composite particles, the porous carrier is not completely encapsulated by the envelope material, and at least 10% of the outer surfaces of the composite particles are formed by the porous carrier.

2. Composite particles according to claim 1, wherein at least one envelope material is a mucoadhesive envelope material, an envelope material having antibacterial effect, an envelope material having antimicrobial effect, or a combination thereof.

3. Composite particles according to claim 1, wherein at least one envelope material releases an active ingredient following activation in the oral chamber.

4. Composite particles according to claim 1, wherein the particles comprise at least one mucoadhesive envelope material and at least one non-mucoadhesive envelope material.

5. Composite particles according to claim 1, wherein the envelope material is an envelope material selected from polysaccharides, poly(meth)acrylates, polyelectrolytes, and fatty acids.

6. Composite particles according to claim 1, wherein at least one active ingredient has antibacterial, antimicrobial, odorizing or flavoring properties.

7. Process for producing composite particles according to claim 1, wherein at least one porous carrier of amorphous $SiO_2$ is contacted with at least one envelope material or with at least one active ingredient and at least one envelope material.

8. Process according to claim 7, wherein at least one active ingredient is contacted with the porous carrier of amorphous $SiO_2$ in such a way that the active ingredient is drawn into the pores of the porous carrier.

9. Process according to claim 1, comprising the following steps:
   a) introducing at least one porous carrier of amorphous $SiO_2$ in a solids mixing unit
   g) adding at least one envelope material
   h) impregnating the porous carrier with at least one envelope material.

10. Process according to claim 9, further comprising at least one of the following steps:
   b) evacuating the solids mixing unit
   c) preimpregnating the porous carrier with at least one envelope material up to a maximum of 50% by weight of the DBP absorption value
   d) adding at least one active ingredient to the solids mixing unit
   e) impregnating the porous carrier with active ingredient
   i) washing, drying, or a combination thereof
   f) inhibiting the active ingredient adhering to the outer particle surface of the porous carrier, washing, drying, or a combination thereof
   j) reactively inhibiting the active ingredient adhering to the outer particle surface of the porous carrier, washing, drying, or a combination thereof.

11. Process according to claim 10, wherein steps b) to e), steps g) to h), or a combination thereof, are carried out repeatedly, it being possible, on repetition of steps d) and e), steps g) and h), or a combination thereof, to use identical or different active ingredients, envelope materials, or a combination thereof in each case.

12. Process according to claim 9, wherein the porous carrier and at least one active ingredient are mixed before being introduced into the solids mixing unit.

13. Process according to claim 9, wherein the amount of at least one envelope substance added in step g) is regulated such that the total amount of at least one active ingredient and at least one envelope material added in the production of the composite particles is 50% to 100% by weight of the DBP absorption value of the porous carrier.

14. Process according to claim 9, wherein the amount of at least one envelope material added in step g) is regulated such that the total amount of at least one active ingredient and at least one envelope material added in the production of the composite particles is greater than the total pore volume of the porous carrier, and the excess of at least one envelope material is absorbed by addition of porous carrier, porous carrier charged with at least one active ingredient, or a combination thereof.

15. Process according to claim 7, wherein the envelope material is a polysaccharide which is gelled following application to the porous carrier.

16. Oral hygiene article comprising at least one composite particle according to claim 1.

17. Oral hygiene article according to claim 16, wherein the article is selected from toothpaste and mouthwash.

18. Method of producing an article for oral hygiene, comprising incorporating composite particles according to claim 1 into the article.

19. Method according to claim 18, wherein the article is selected from toothpaste and mouthwash.

* * * * *